(12) United States Patent
Ott et al.

(10) Patent No.: US 12,352,603 B2
(45) Date of Patent: Jul. 8, 2025

(54) CULTIVATION SYSTEM AND CONTAINER ATTACHMENT FOR CULTIVATION CONTAINER

(71) Applicant: SCHOTT AG, Mainz (DE)

(72) Inventors: Christian Ott, Ampfing (DE); Christoph Kolberg, Landshut (DE)

(73) Assignee: SCHOTT AG, Mainz (DE)

( * ) Notice: Subject to any disclaimer, the term of this patent is extended or adjusted under 35 U.S.C. 154(b) by 906 days.

(21) Appl. No.: 16/915,494

(22) Filed: Jun. 29, 2020

(65) Prior Publication Data

US 2021/0147774 A1    May 20, 2021

(30) Foreign Application Priority Data

Jun. 27, 2019   (DE) ............... 10 2019 117 446.5

(51) Int. Cl.
| | | |
|---|---|---|
| C12M 1/24 | (2006.01) | |
| C12M 1/00 | (2006.01) | |
| C12M 1/34 | (2006.01) | |
| C12M 3/00 | (2006.01) | |
| G01D 5/26 | (2006.01) | |
| G01D 11/24 | (2006.01) | |
| G01D 11/26 | (2006.01) | |

(52) U.S. Cl.
CPC ........... *G01D 11/245* (2013.01); *C12M 23/00* (2013.01); *C12M 23/08* (2013.01); *C12M 23/48* (2013.01); *C12M 41/06* (2013.01); *C12M 41/30* (2013.01); *G01D 5/268* (2013.01); *G01D 11/26* (2013.01)

(58) Field of Classification Search
None
See application file for complete search history.

(56) References Cited

U.S. PATENT DOCUMENTS

| | | | | |
|---|---|---|---|---|
| 6,903,823 | B1 * | 6/2005 | Muller | G01N 33/497 |
| | | | | 435/39 |
| 2005/0058986 | A1 * | 3/2005 | Sullivan | C12Q 1/04 |
| | | | | 435/5 |
| 2005/0255584 | A1 * | 11/2005 | Broneske | C12M 21/02 |
| | | | | 435/293.1 |
| 2010/0035337 | A1 | 2/2010 | Bahnemann | |
| 2012/0097557 | A1 | 4/2012 | Baumfalk | |
| 2013/0039810 | A1 | 2/2013 | Riechers | |
| 2015/0218501 | A1 | 8/2015 | Kauling | |
| 2016/0305897 | A1 | 10/2016 | Furey | |
| 2017/0219512 | A1 | 8/2017 | Wunderlich | |
| 2018/0155667 | A1 | 6/2018 | Stobbe | |
| 2020/0071654 | A1 | 3/2020 | Heo | |

FOREIGN PATENT DOCUMENTS

| | | | | |
|---|---|---|---|---|
| CA | 2884865 | * | 3/2014 | ............. C12M 3/00 |
| CN | 201658978 | | 12/2010 | |
| CN | 202297585 | | 7/2012 | |
| CN | 108018204 | | 5/2018 | |
| DE | 19819857 | | 11/1998 | |
| DE | 202009010255 | | 10/2009 | |
| DE | 102009037345 | | 12/2010 | |
| DE | 102010007559 | | 8/2011 | |
| DE | 102013015106 | | 3/2015 | |
| DE | 202016000554 | | 5/2017 | |
| DE | 102016101715 | | 8/2017 | |
| EP | 2371942 | | 10/2011 | |
| EP | 3109314 | | 12/2016 | |
| JP | H06141850 | | 5/1994 | |
| JP | 2007202542 | | 8/2007 | |
| JP | 2018534940 | A | 11/2018 | |
| WO | 9008816 | | 8/1990 | |
| WO | 2014044612 | | 3/2014 | |
| WO | WO2018035399 | * | 2/2018 | ............. G01N 33/49 |
| WO | 2018037402 | | 3/2018 | |
| WO | 2018082552 | | 5/2018 | |
| WO | 2018097510 | | 5/2018 | |

\* cited by examiner

*Primary Examiner* — Ann Montgomery
(74) *Attorney, Agent, or Firm* — Ruggiero McAllister & McMahon LLC

(57) ABSTRACT

The invention relates to a cultivation system comprising a cultivation container, in particular a hand-held cultivation container, preferably in the form of a shake flask, for holding a culture medium, the cultivation container having a neck and an opening extending through the neck, and a container attachment that can be placed on the neck of the cultivation container so as to close the opening of the cultivation container, in particular in a sterile manner, the container attachment having an inner side and an outer side, the inner side facing the interior of the cultivation container and the outer side facing the exterior of the cultivation container when the container attachment is placed on the neck of the cultivation container, wherein the container attachment comprises at least one sensor unit or a port for installing a sensor unit, the sensor unit being at least partially arranged or arrangeable on the inner side of the container attachment, to provide for parameter measurement in the interior of the cultivation container, and/or wherein the container attachment comprises at least one dispensing unit or a port for installing a dispensing unit, the dispensing unit being at least partially arranged or arrangeable on the inner side of the container attachment, to enable liquid to be dispensed into the interior of the cultivation container.

21 Claims, 7 Drawing Sheets

CULTIVATION SYSTEM AND CONTAINER ATTACHMENT FOR CULTIVATION CONTAINER

CROSS REFERENCE TO RELATED APPLICATIONS

This application claims benefit under 35 USC § 119 of German Application No. 10 2019 117 446.5 filed Jun. 27, 2019, the entire contents of which are incorporated herein by reference.

BACKGROUND

Field of the Invention

The invention relates to a cultivation system comprising a container attachment for a cultivation container, in particular a hand-held cultivation container such as a shake flask.

Description of Related Art

Bioreactors and shake flasks are used to cultivate microorganisms, animal and plant cells, and thus open up a wide range of applications for biotechnological production processes. Generally, there is a need to further optimize such processes. In particular for the production of biopharmaceuticals, improvements in product yield and hence profit growth are being pushed. Various approaches are available to control and monitor the production processes, to increase product yield, and to reduce costs.

Generally, the processes can be controlled and monitored by determining substrate and product concentrations. However, this is time-consuming and usually requires resource-intensive offline analysis. Due to the sampling, this is also associated with a not negligible risk of contamination.

If conventional bioreactors are used, process control and thus yield can be optimized by performing real-time process control of key parameters. Particularly advantageous for increasing product yield is in-situ monitoring of parameters such as temperature, substances relevant to metabolism or product formation, as well as feedback control of cultivation conditions in real time.

However, if shake flasks or other hand-held cultivation containers are used, sampling has so far been necessary, which poses a risk of contamination due to the handling when the cultivation unit is open. Moreover, because of the offline analysis, sampling is time-consuming, as is the determination of substrate and product concentrations.

Sampling my also mean that the interruption of the mixing process performed by a shaking incubator stops the exchange of substances, in particular that of dissolved gases, thereby inhibiting cultivation. In addition, the many hours of reaction can interfere with pH corrections or substrate feed, which is due to the duration of the off-line analysis. Furthermore, the risk of contamination increases with each opening of the shake flask.

Metabolism usually produces pH-lowering metabolites. Attempts to counteract this sometimes include buffering of the medium. In particular during process development, pH controls and feeds for pH adjustment may be necessary when the buffer capacity is exhausted. Medium constituents should not be presented in any arbitrary concentration at the beginning of the cultivation, since this might lead to undesired substrate inhibition.

In order to reduce the repetitions of sampling when using a shake flask, there have been approaches involving the measuring of optical density and luminescence from glue-mounted spots, for example for pH and $pO_2$.

However, the optical quality of the shake flask wall (e.g. transmittance, scattering) limits this principle. It should also be noted that the detection of cell growth via optical density requires a constant extinction coefficient. However, the latter varies with the medium composition which is changing during cultivation. This creates a difference between vital and lysed cells. Another limitation in the case of glue-mounted spots is caused by what is known as "leaching" and "drift".

Therefore, an object of the invention is to make cultivations involving shake flasks or other hand-held cultivation containers as efficient as bioreactors and at the same time minimize the requirements on the periphery, for example to avoid the need for a sterile workbench. A general aspect of the object of the invention is to make biotechnological production processes more cost-effective and to enable a more agile application.

To this end, the invention discloses a cultivation system which comprises a cultivation container, in particular a hand-held cultivation container, for holding a culture medium, and a container attachment which can be placed on the cultivation container.

The cultivation container which is preferably in the form of a shake flask has a neck and an opening extending through the neck. Preferably, the opening is the only access to the interior of the cultivation container, that is to say the cultivation container preferably has no further port.

The container attachment can be placed on the neck of the cultivation container so as to close the opening of the cultivation container, in particular in a sterile sealing manner. When the container attachment is placed on the neck of the cultivation container, an inner side of the container attachment faces the interior of the cultivation container, i.e. in particular the sterile area, and an outer side of the container attachment faces the exterior of the cultivation container, i.e. in particular the non-sterile area.

The container attachment is characterized by comprising at least one sensor unit or a port for installing a sensor unit and/or by comprising a dispensing unit or a port for installing a dispensing unit.

The optionally comprised sensor unit is at least partially arranged or arrangeable on the inner side of the container attachment, to provide for parameter measurement in the interior of the cultivation container. The sensor unit may be firmly attached on the inner side of the container attachment, for example.

Otherwise, the sensor unit may also be arranged or installed on the inner side of the cultivation container so that in particular a modular exchange is possible, for example by installing a sensor component or a multi-sensor component on a corresponding port of the container attachment. In this regard, reference is made in particular to German patent application 10 2019 117 446.5 which is incorporated herein by reference.

The optionally comprised dispensing unit is likewise at least partially arranged or arrangeable on the inner side of the container attachment, in order to enable liquid to be dispensed into the interior of the cultivation container. The dispensing unit may likewise be firmly attached to the container attachment, in particular completely or at least partially on the inner side of the container attachment so as to allow liquid to be dispensed into the interior of the container.

Otherwise, the dispensing unit, i.e. at least a section of the dispensing unit, may also be arranged or installed on the inner side of the cultivation container so that in particular a modular exchange is possible, for example by installing the dispensing unit in a corresponding port of the container attachment.

While a sensor unit allows to capture and optionally process key parameters for process control in real time, a dispensing unit provides for active corrections, e.g. pH correction or feed rate. If parameter deviations from the target value are beyond intervention limits, actuators can be actively controlled, for example, such as for pH correction or feed rate. Since the container attachment comprises a sensor unit or a respective port and/or a dispensing unit or a respective port, this allows for integration of sensors and/or actuators such that in particular autonomous cultivation systems with closed control loops can be implemented, for optimized cultivation conditions. If both a sensor unit and a dispensing unit are provided or installed, a CAP (Controlled and Adjusted Process) system is thus created, which in particular enables demand-oriented use of sensors and actuators in a system.

The invention, that is a CAP cultivation system in particular comprising a hand-held cultivation container or a shake flask, drastically reduces the requirements on the periphery, in particular compared to conventional bioreactors. Sometimes a shaking incubator and an autoclave may be sufficient. Even a sterile workbench can optionally be avoided, in which case in particular sterile connectors can be provided, as will be explained in more detail below. The aspects mentioned above increase cost efficiency and allow for both a broader and more agile application. The invention makes it possible for the cultivation conditions to continuously be kept within the optimal range. Deviations in parameters can be counteracted instantly. The invention provides a cultivation system with a performance comparable to that of a bioreactor.

The cultivation container may in principle have any desired shape, for example it may be shaped like a conventional bioreactor (optionally with flow breakers) with straight side walls. However, hand-held cultivation containers are preferred, in particular shake flasks. Reasons for this are availability and design, for example, and one design feature may be the material and heat transfer which can be influenced in particular through the number of baffles.

The cultivation container has a neck, which preferably has an annular, in particular cylindrical shape. Correspondingly, the container attachment may have an annular, in particular cylindrical slot for accommodating the neck of the cultivation container.

Furthermore, the container attachment may have an outer collar forming part of the outer side of the container attachment and radially surrounding the neck of the cultivation container when the container attachment is placed on the neck of the cultivation container. The container attachment may also have an inner projection forming part of the inner side of the container attachment and protruding into the opening which extends through the neck of the cultivation container when the container attachment is placed on the neck of the cultivation container. The outer collar and the inner projection of the container attachment may be formed monolithically, i.e. integrally. In other words, the outer collar is in particular not designed to be rotatable with respect to the inner projection.

The cultivation container may have a flat base for being placed on a supporting surface. The neck of the cultivation container may extend vertically upwards, for example, in particular when the cultivation container is placed on the supporting surface. Accordingly, the container attachment may be designed for being placed onto the neck of the cultivation container vertically from above, and may furthermore preferably be designed to be held on the neck of the cultivation container by gravity.

The container attachment that can be placed on the cultivation container preferably has an abutment surface that comes to rest on the cultivation container when the container attachment is placed on the cultivation container. The abutment surface is in particular located inside the slot provided in the container attachment, in particular the annular slot for receiving the neck of the cultivation container. In other words, the container attachment with its abutment surface is in particular supported on the upper end of the neck when the container attachment is placed on the cultivation container.

The cultivation container in particular has a volume of less than 2801 milliliters, preferably less than 1801 milliliters, more preferably less than 501 milliliters, even more preferably less than 251 milliliters, and most preferably of less than 126 milliliters.

Furthermore, the cultivation container may have a diameter of less than 22 centimeters or less than 21 centimeters, preferably of less than 14 centimeters or less than 12 centimeters, most preferably less of than 9 centimeters or less than 8 centimeters.

The cultivation container may have a height of less than 31 centimeters, preferably less than 23 centimeters, more preferably less than 19 centimeters, yet more preferably less than 17 centimeters, most preferably less than 14 centimeters.

The container attachment that can be placed on the cultivation container preferably has a height, as measured from the abutment surface, of less than 10 centimeters, preferably less than 5 centimeters, more preferably less than 4 centimeters, yet more preferably less than 3 centimeters, most preferably less than 2 centimeters. In other words, the container attachment, in its fitted state, implies an increase in height of the cultivation container by at most the specified values.

As mentioned before, the container attachment preferably comprises one or more dispensing units which serve to control process parameters. The at least one dispensing unit of the container attachment preferably comprises a reservoir for holding liquid, and such reservoir comprises a lower reservoir section having an outlet opening for dispensing liquid and preferably an upper reservoir section having a post flow opening for post flow of gas.

The lower reservoir section is preferably arranged or arrangeable on the inner side of the container attachment, in order to allow liquid to be dispensed through the outlet opening into the interior of the cultivation container, and the upper reservoir section is preferably arranged or arrangeable on the outer side of the container attachment and is particularly preferably designed so as to have a larger width in order to define a stop when the dispensing unit and/or the reservoir is installed on a port of the container attachment.

The container attachment and/or the dispensing unit may comprise a connection, in particular in the form of a flexible tube, between the post flow opening of the upper reservoir section and the inner side of the container attachment, in order to provide for post flow of gas, in particular in a sterile manner, from the interior of the cultivation container when the container attachment is placed on the neck of the cultivation container.

The reservoir, in particular the upper reservoir section, may furthermore have a refill opening for refilling liquid, and the container attachment and/or the dispensing unit preferably comprise a connection, in particular in the form of a flexible tube, between the refill opening of the reservoir and a valve that is arranged or arrangeable on the outer side of the container attachment, to enable liquid to be refilled into the reservoir, in particular in a sterile manner. The container attachment and/or the dispensing unit may furthermore have a bracket for releasably fixing the valve, which is attached on a radial outer side, for example.

In order to provide for feed into or extraction from the interior of the cultivation container, in particular in a sterile manner, when the container attachment is placed on the neck of the cultivation container, the container attachment may furthermore comprise a connection, in particular in the form of a flexible tube, between the inner side of the container attachment and a valve that is arranged or arrangeable on the outer side of the container attachment. For this purpose, the container attachment may again have a bracket for releasably fixing the valve, which is attached on a radial outer side, for example.

The at least one sensor unit of the container attachment may in particular be in the form of a biosensor unit for analyte-specific parameter measurement. An analyte-specific parameter measurement may imply that a particular parameter, the analyte, is selectively captured, i.e. in particular a plurality of parameters, e.g. different analytes, are not captured at the same time.

Otherwise, the at least one or a further sensor unit of the container attachment, which is in particular not a biosensor unit, may be in the form of a luminophoric unit for luminescence-based parameter measurement. With luminescence-based parameter measurement, analyte-dependent signal quenching may be effected. The excitation wavelength may be offset in wavelength and/or phase due to the interaction with the measured parameter.

The at least one or a further sensor unit may also be in the form of an alternating field unit for dielectric-based parameter measurement. If charges move in the electric field in analytes, a dipole is induced. In the case of a dielectric-based measurement, this frequency-dependent interaction may be exploited in a sensor unit.

The at least one or a further sensor unit may also be in the form of a transistor unit for field effect-based parameter measurement. In this case, ionic analytes may cause a mirror charge in a semiconductor element, which generates conductivity, in particular by reversibly attaching to a sensor chip in an ion-selective manner.

With regard to the sensor unit, reference is made to German patent application 10 2019 117 446.5. Accordingly, the at least one sensor unit may be arranged or arrangeable on a front housing section of a sensor component, in particular a multi-sensor component, such that the at least one sensor unit is arrangeable on the inner side of the container attachment by installing the sensor component on a port of the container attachment to enable parameter measurement in the interior of the cultivation container when the container attachment is placed on the neck of the cultivation container. A multi-sensor component permits to install a plurality sensor units at the same time.

The container attachment preferably comprises a plurality of sensor and/or dispensing units or corresponding ports, in particular at least one sensor unit or a corresponding port and at least one dispensing unit or a corresponding port, particularly preferably, selectively, at least one sensor unit or a corresponding port and at least two dispensing units or corresponding ports.

In addition to the cultivation system comprising the cultivation container and container attachment as described above, the invention furthermore relates to the container attachment for being placed on a cultivation container, in particular a hand-held cultivation container, preferably a shake flask.

The container attachment comprises an inner side facing the interior of the cultivation container when the container attachment is placed on the cultivation container, and an outer side facing the exterior of the cultivation container when the container attachment is placed on the cultivation container.

Furthermore, the container attachment comprises at least one sensor unit or a port for installing a sensor unit and/or at least one dispensing unit or a port for installing a dispensing unit. At least a section of the sensor unit is arranged or arrangeable on the inner side of the container attachment in order to provide for parameter measurement in the interior of the cultivation container. Also, at least a section of the dispensing unit is arranged or arrangeable on the inner side of the container attachment in order to enable liquid to be dispensed into the interior of the cultivation container.

The container attachment may have an annular, in particular cylindrical slot for receiving a neck of the cultivation container. Furthermore, the container attachment may have an outer collar which radially surrounds the neck of a cultivation container when the container attachment is placed on a cultivation container. Furthermore, the container attachment may have an inner projection protruding into the neck of a cultivation container when the container attachment is placed on a cultivation container. The outer collar and the inner projection may be monolithic, i.e. integrally formed.

The container attachment is in particular designed to be placed onto a cultivation container vertically from above and is preferably designed to be held on the cultivation container by gravity.

The container attachment preferably has an abutment surface which comes to rest on the cultivation container when the container attachment is placed on the cultivation container, and the abutment surface is in particular located inside the slot provided in the container attachment, in particular the annular slot for receiving the neck of the cultivation container.

The container attachment that can be placed on the cultivation container preferably has a height, as measured from the abutment surface, of less than 10 centimeters, preferably less than 5 centimeters, yet more preferably less than 4 centimeters, even more preferably less than 3 centimeters, most preferably less than 2 centimeters.

The at least one dispensing unit of the container attachment may comprise a reservoir for holding liquid, which reservoir comprises a lower reservoir section with an outlet opening for dispensing liquid and preferably an upper reservoir section with a post flow opening for post flow of gas.

The lower reservoir section is preferably arranged or arrangeable on the inner side of the container attachment in order to allow liquid to be dispensed through the outlet opening into the interior of the cultivation container. The upper reservoir section is preferably arranged or arrangeable on the outer side of the container attachment and is particularly preferably designed to have a larger width in order to define a stop when the dispensing unit and/or the reservoir is installed on a port of the container attachment.

The container attachment and/or the dispensing unit may have a connection between the post flow opening of the upper reservoir section and the inner side of the container attachment in order to allow gas to flow in from the interior of the cultivation container when the container attachment is placed on the cultivation container.

Furthermore, the reservoir may have a refill opening for refilling liquid, and the container attachment and/or the dispensing unit preferably comprises a connection between the refill opening of the reservoir and a valve arranged or arrangeable on the outer side of the container attachment, to enable liquid to be refilled into the reservoir. The container attachment and/or the dispensing unit may have a bracket for releasably fixing the valve.

In order to provide for feed into or extraction from the interior of the cultivation container when the container attachment is placed on the cultivation container, the container attachment may furthermore comprise a connection between the inner side of the container attachment and a valve which is arranged or arrangeable on the outer side of the container attachment. For this purpose, the container attachment may also comprise a bracket for releasably fixing the valve.

The at least one sensor unit of the container attachment may be a biosensor unit for analyte-specific parameter measurement. Otherwise, the at least one sensor unit or a further sensor unit of the container attachment, which in particular is not a biosensor unit, may be a luminophoric unit for luminescence-based parameter measurement. The at least one or a further sensor unit may also be an alternating field unit for dielectric-based parameter measurement. The at least one or a further sensor unit may also be a transistor unit for field effect-based parameter measurement. In particular referring to German patent application 10 2019 117 446.5, the at least one sensor unit may be arranged or arrangeable on a front housing section of a sensor component such that the at least one sensor unit is arrangeable on the inner side of the container attachment by installing the sensor component on a port of the container attachment.

In a preferred embodiment, the container attachment comprises a plurality of sensor and/or dispensing units or corresponding ports, in particular at least one sensor unit or a corresponding port and at least one dispensing unit or a corresponding port, particularly preferably at least one sensor unit or a corresponding port and at least two dispensing units or corresponding ports.

The invention furthermore relates to a dispensing unit for being installed on a port of a container attachment, in particular as described above, which dispensing unit comprising a reservoir for holding liquid, which reservoir comprises a lower reservoir section with an outlet opening for dispensing liquid and preferably an upper reservoir section with a post flow opening for post flow of gas.

The reservoir may have a refill opening for refilling liquid, and a connection may also be provided between the refill opening of the reservoir and a valve in order to enable liquid to be refilled into the reservoir, in particular in a sterile manner.

The liquids in the reservoirs and in the medium are preferably matched to one another so as to allow to cover the large variety of cultivations in life sciences. For example, a feed solution in the reservoir may contain the substrates required for product formation, such as saccharides. Since cell metabolism may bring about pH-lowering medium constituents such as organic acids, a pH-increasing correction solution may preferably be provided, which may contain NaOH, for example. Thus, a pH correction solution may be provided in the reservoir. A pH correction solution in the reservoir in particular allows to provide a buffer system with the medium. For example, cell metabolism forms $CO_2$ and thus $H_2CO_3$, and a $HCO_3$ correction solution provides a buffer system with readjusted buffer capacity and stable pH value.

Furthermore, it is also possible to provide a feed solution including pH correction. In particular stoichiometry can show how much pH-lowering substances are formed by the metabolism of the feed. Accordingly, the pH correction can be metered in with the feed solution, taking into account the substrate turnover rate and buffer effect in the medium. This makes it possible, for example, to form biomass by dosing using a first reservoir, and to optimize product formation by dosing using a further reservoir.

The invention accordingly furthermore relates to a method for propagation or cultivation of biological material, preferably for the production of pharmaceuticals, in particular biopharmaceuticals, comprising the method steps of: providing a cultivation system, in particular as described above, which comprises a cultivation container and at least one reservoir with a respective outlet opening for dispensing liquid into the interior of the cultivation container; providing a feed solution, in particular containing the substrates required for product formation, e.g. saccharides, wherein the feed solution is preferably provided in the reservoir; providing a pH correction solution, especially for raising the pH value, e.g. containing NaOH, wherein the pH correction solution is preferably provided in a further reservoir and/or is provided included in the feed solution.

The invention furthermore relates to a method for propagation or cultivation of biological material, preferably for the production of pharmaceuticals, in particular biopharmaceuticals, comprising the method steps of: providing a plurality of cultivation systems, in particular as described above; connecting the plurality of cultivation systems to a pump module, via a flexible feed/extraction tube, and preferably automatically inoculating the plurality of cultivation systems.

An extended use of the described cultivation system may in particular be useful for modularization and process intensification. In particular a plurality of the described cultivation systems may be used, each of which represents a standardized bioprocess module which allows for flexible adaptation to desired requirements. In addition to parallel cultivations, these are examples of implementation of strategies for process intensification, implying an efficient increase in space-time yields. This is preferably achieved by replacing a conventional cryostock vail by a cryostock syringe which is used to directly inoculate a prepared cultivation system via a feed/extraction tube (more precisely: a valve connected thereto), in particular in a sterile and safe manner. Hence, handling and periphery requirements common in the art can advantageously be eliminated. A CAP (Controlled and Adjusted Process) in a cultivation system of the described type in particular allows for vitalization and log. proliferation of the cells. Additional cultivation systems can be automatically inoculated via a flexible feed/extraction tube (flexible transfer tube) and optionally a pump module. This permits, for example, to process different personalized biopharmaceuticals in an incubation shaker. If additional cultivation systems are connected to each other via automated transfer and medium is re-dosed accordingly into the initial bioprocess module, this allows to implement continuous bioprocesses and thus to achieve process intensification. Even in the event of contamination, the loss is minimal compared to conventional bioprocesses.

Some specific exemplary embodiments of the invention which should not be construed as exhaustive will now be discussed with reference to the accompanying drawings, wherein.

Figure 1:
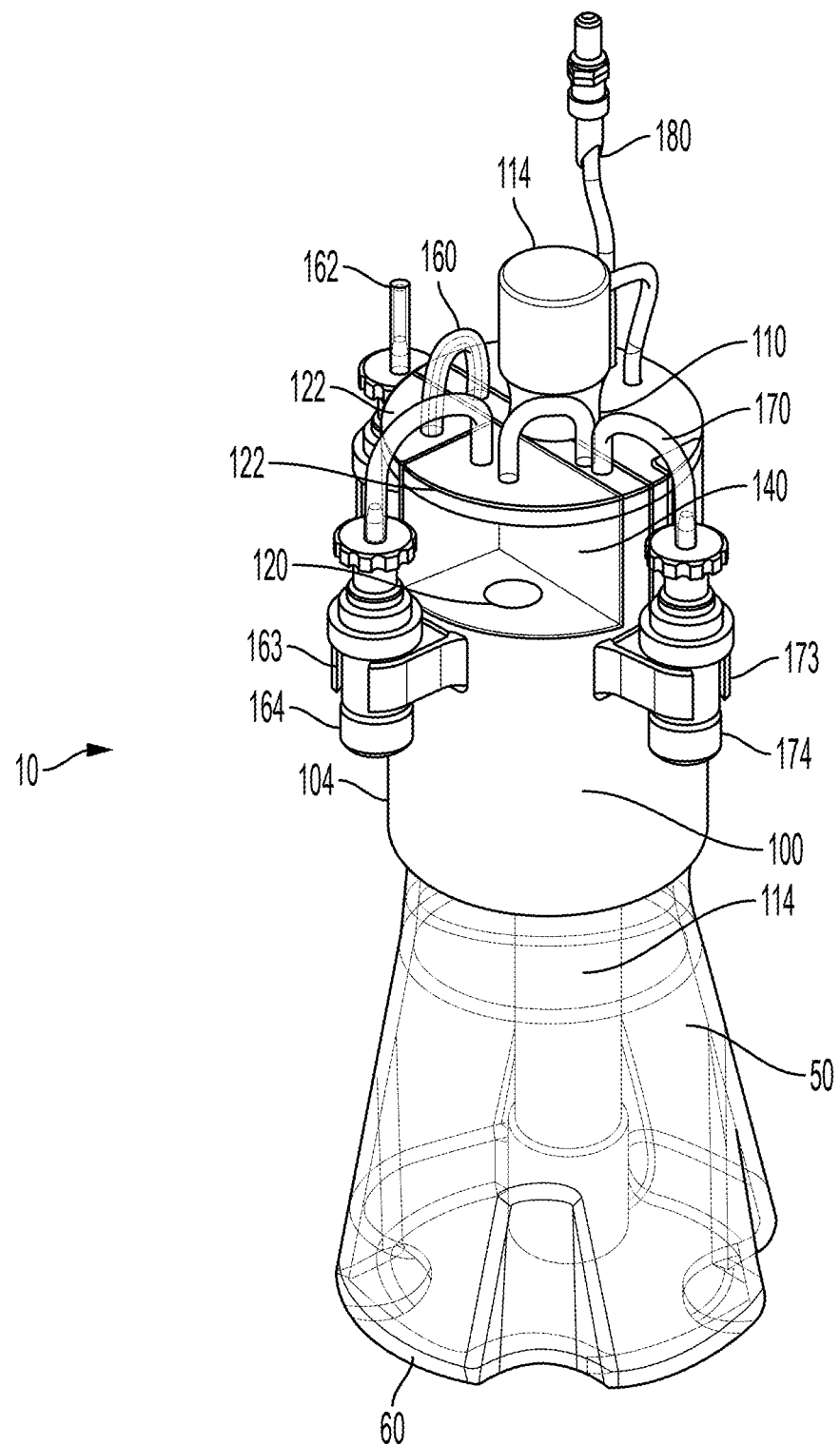
FIG. 1 is a perspective view of a cultivation system.
Figures 2A, 2B:
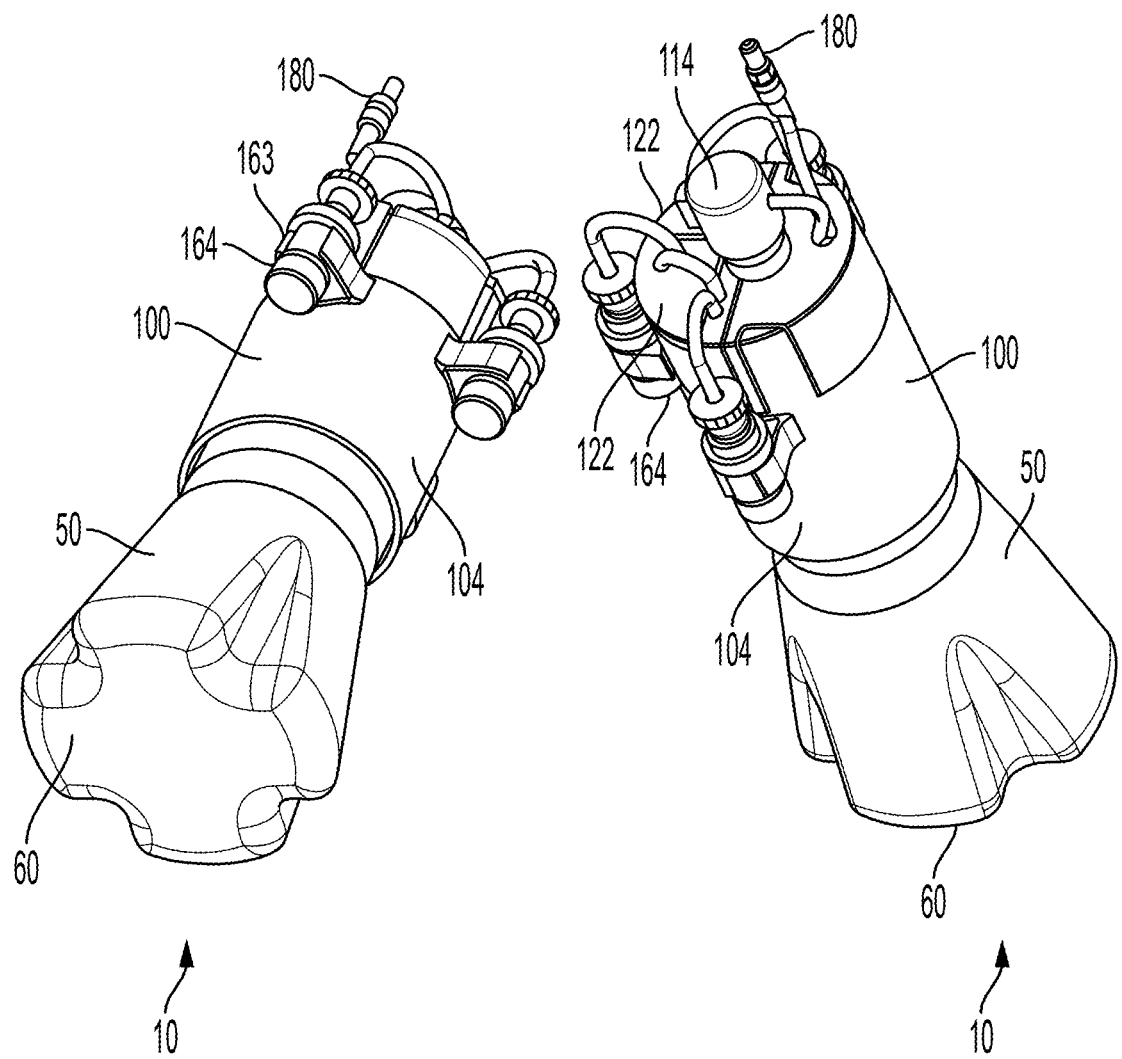
FIGS. 2a and 2b show further perspective views of the cultivation system of FIG. 1.
Figure 3:
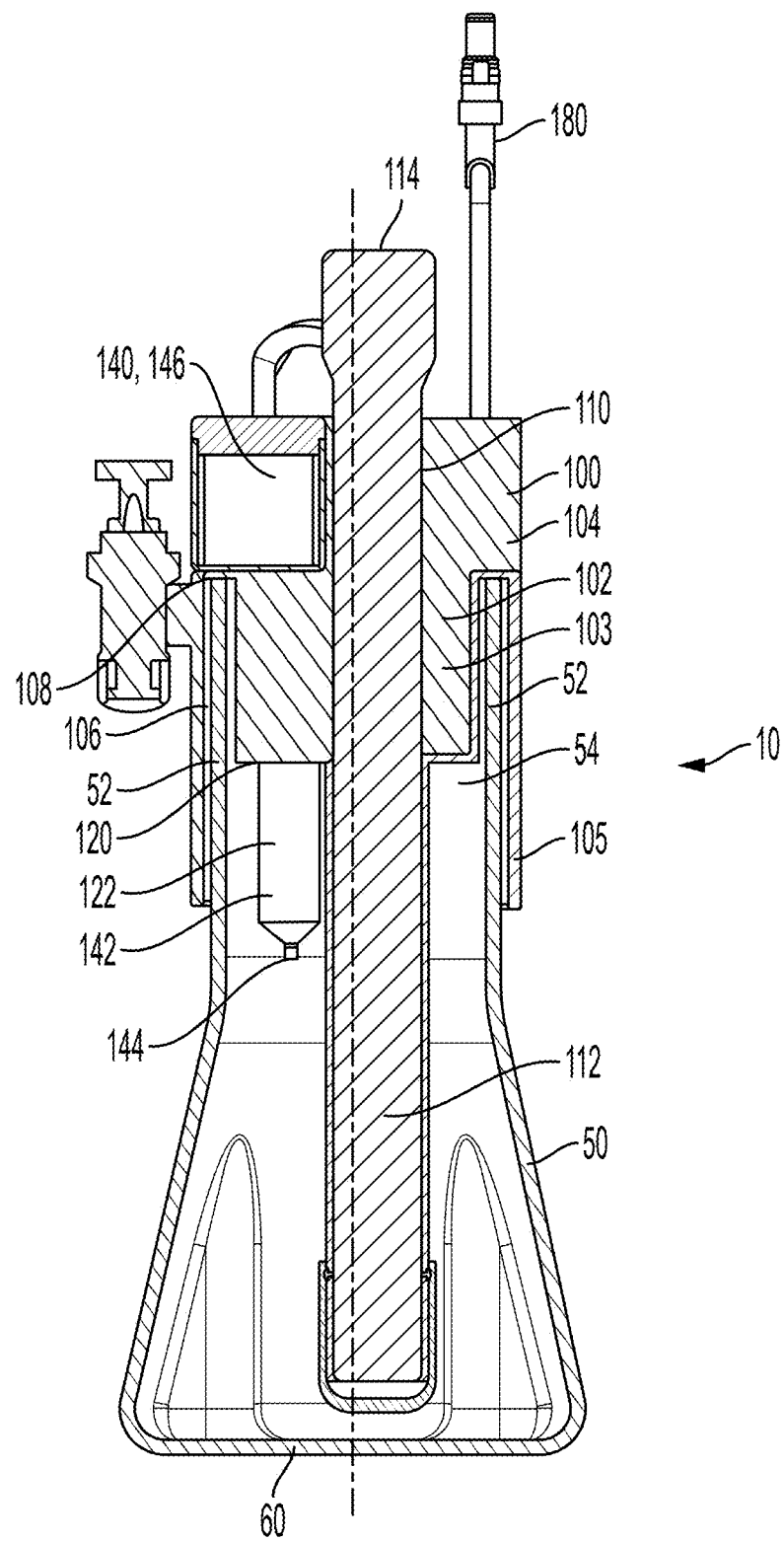
FIG. 3 is a sectional view of the cultivation system of FIG. 1.

Referring to FIGS. 1 to 3, a cultivation system 10 comprises a cultivation container 50, in particular made of glass or polymer, and a container attachment 100.

The container attachment 100 is placed onto the neck 52 of the cultivation container 50 vertically from above (see FIG. 3), and the cultivation container 50 has a flat base 60 so that it can be placed on a supporting surface, so that the neck 52 of the container extends vertically upwards.

The container attachment 100 has an inner side 102 and an outer side 104, the inner side 102 protruding into the opening 54 of the cultivation container 50 extending through the neck 52 and thus facing the interior of the container 50, and the outer side 104 faces the exterior of the container 50.

The container attachment 100 has an annular slot 106 into which the neck 52 of the cultivation container 50 protrudes. In this way, sterile sealing of the cultivation container 50 is enabled. Slot 106 separates the outer collar 105 being part of the outer side 104 from the inner projection 103 being part of the inner side 102 of the container attachment 100 which comprises a monolithic base body, i.e. it is formed unitarily so that in particular the outer collar 105 and the inner projection 103 are formed integrally from one piece of material.

In the illustrated example, the container attachment comprises a port 110 for installing a sensor unit 112, which in this case is accommodated in a multi-sensor component 114 that can be installed on port 110 in a modular manner, and two ports 120 for installing two dispensing units 122.

Figure 5:
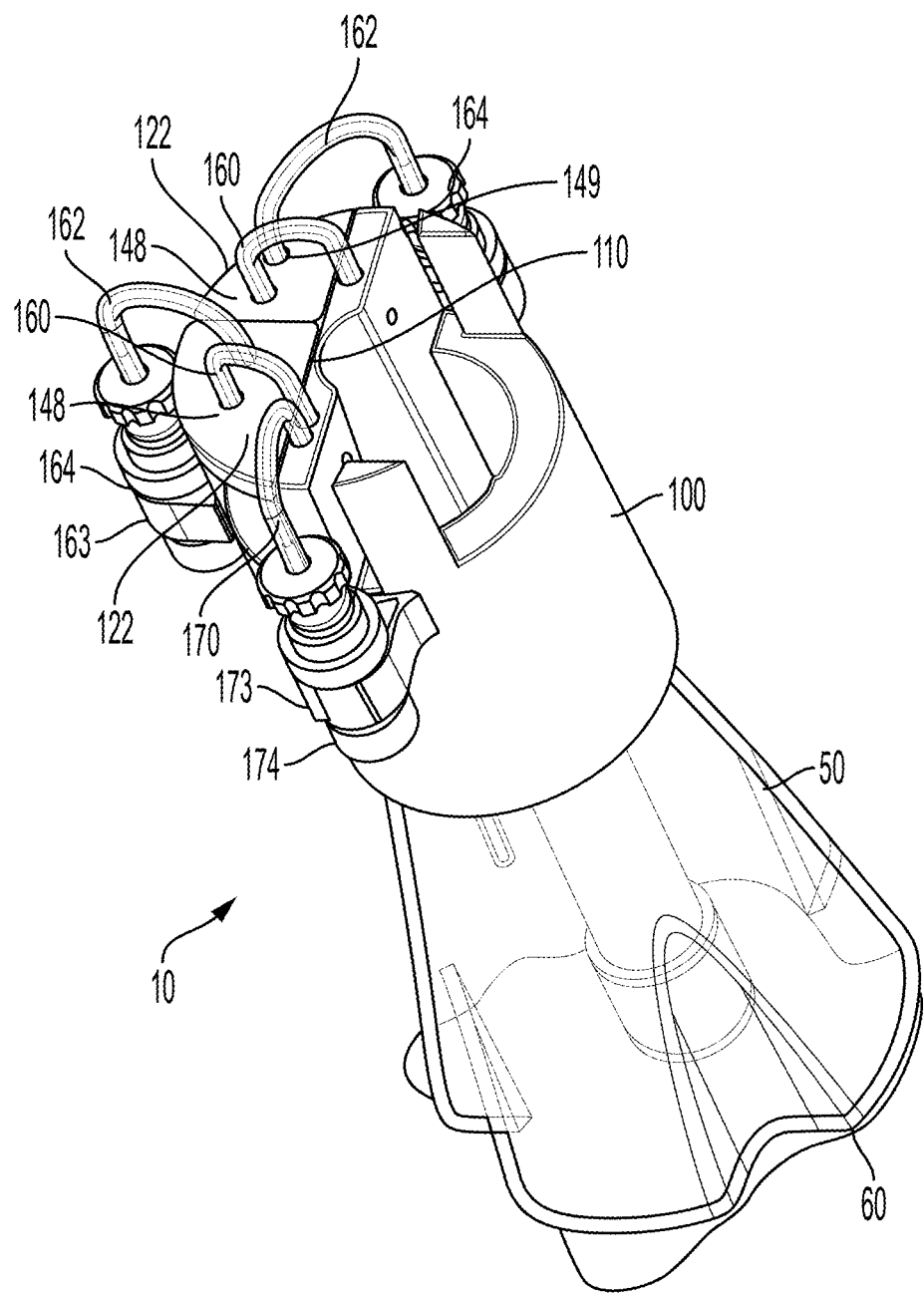
FIG. 5 is a perspective view of a cultivation system.
Figure 6:
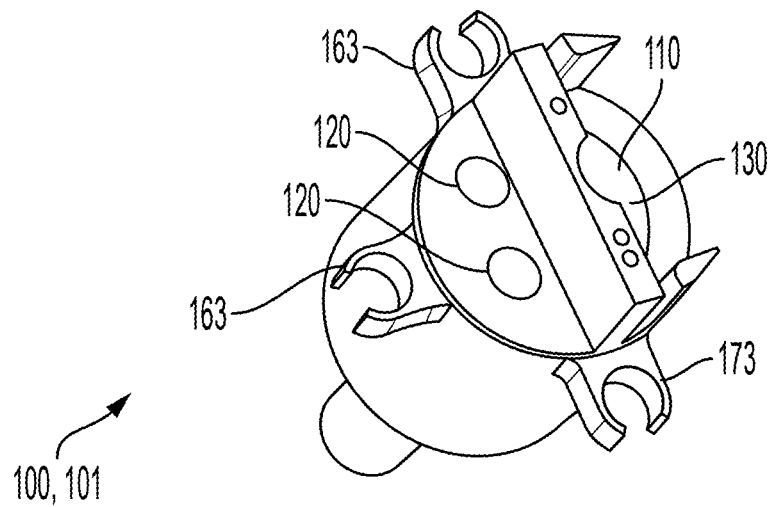
FIG. 6 is a perspective view of a container attachment.
Figure 7:
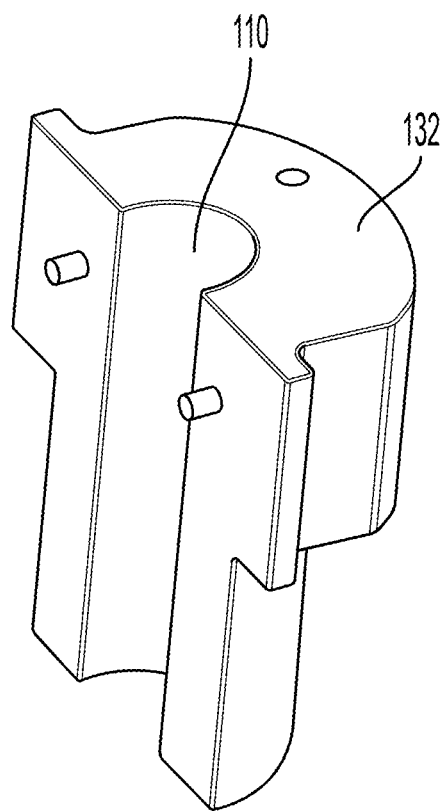
FIG. 7 is a perspective view of an electronic module.

As can be seen from FIGS. 5 to 8, the cultivation system 10 preferably is of modular design, such that, for example, sensor unit 112 and/or dispensing unit 122 can be installed on the container attachment 100 in a modular manner. For example, FIG. 6 shows a container attachment 100 which is in the form of a base body 101 having ports 110, 120 for installing sensor units and dispensing units. The illustrated container attachment also has a port 130 for installing an electronic module 132 (see FIG. 7) which in turn defines part of the port 110 for installing a sensor unit 112 or a (multi-) sensor component 114.

Figure 8:
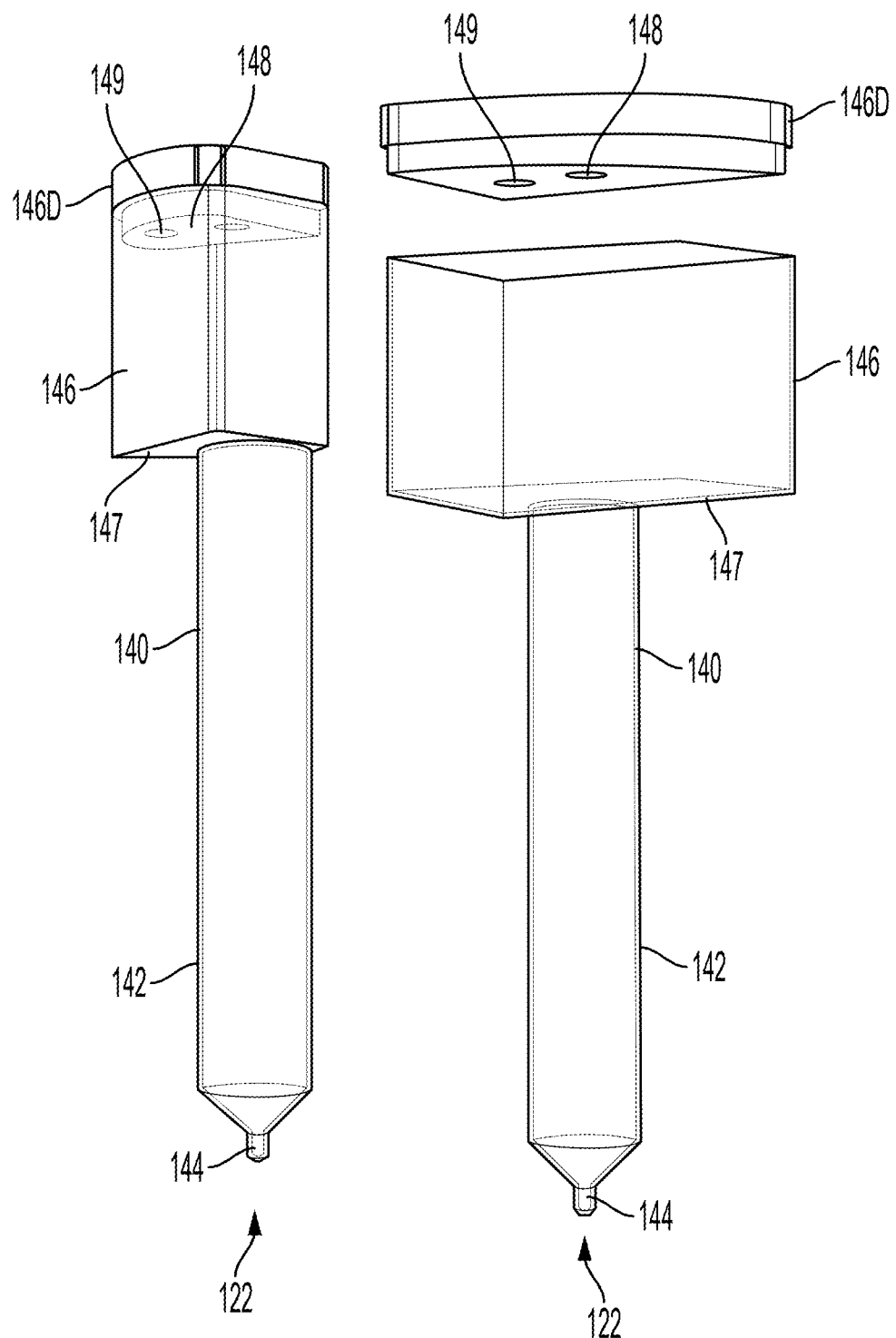
FIG. 8 is a perspective view of two dispensing units.

Referring to FIG. 8, the dispensing unit 122 of the container attachment 100 comprises a reservoir 140, in particular for a feed and pH adjustment substance. Reservoir 140 comprises a lower reservoir section 142 having an outlet opening 144, and an upper reservoir section 146 having a post flow opening 148 for post flow of gas. The upper reservoir section 146 has a larger width than the lower reservoir section 142 thereby defining a stop 147 for the modular installation of the dispensing unit 122. The upper reservoir section 146 furthermore has a refill opening 149 for refilling liquid into the reservoir 140.

Figure 4:
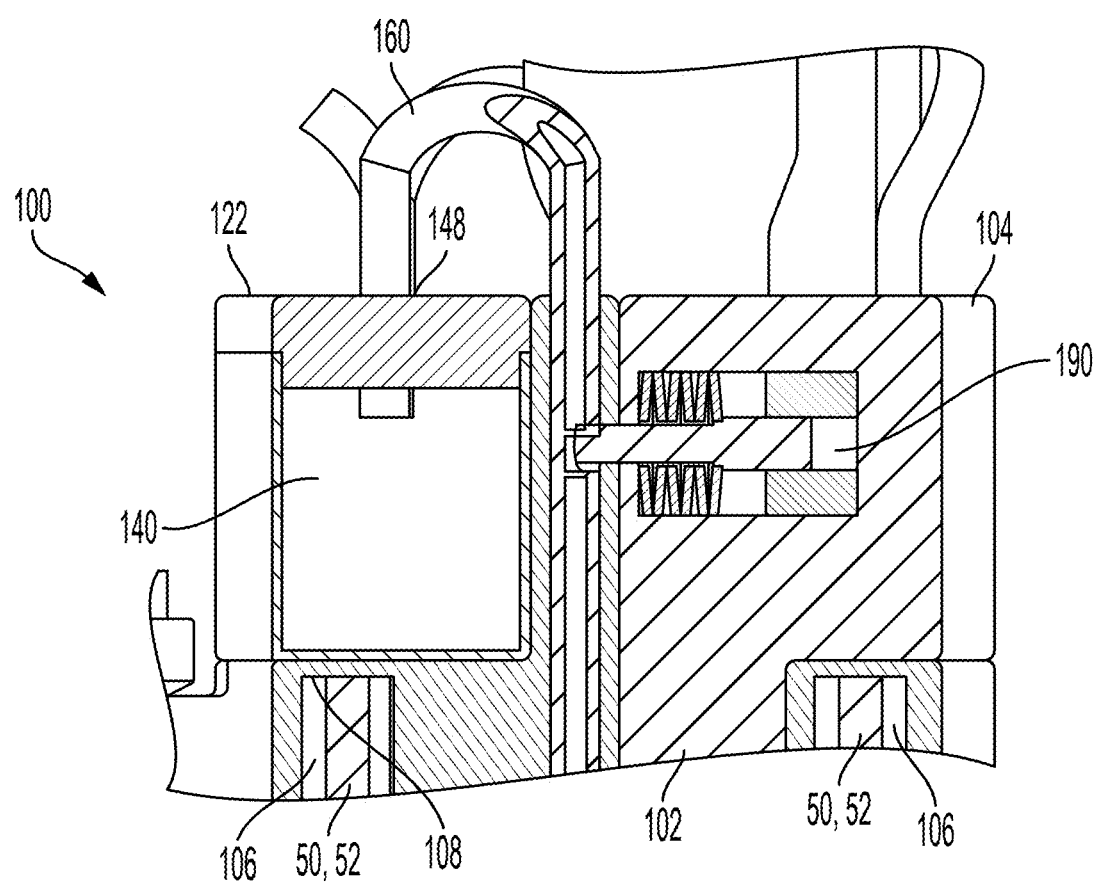
FIG. 4 shows a further sectional view of the cultivation system of FIG. 1.

As can be best seen from FIGS. 4 and 5, a flexible tube 160 is provided which extends from the post flow opening 148 to the inner side 102 of container attachment 100 and thus into the interior of the cultivation container 50. This provides for sterile post flow of gas from the interior of the container. Furthermore, this provides for pressure-controlled dosing of feed or pH adjustment, as will be explained further below.

A further flexible tube 162 is provided in order to connect the refill opening 149 to a valve 164 attached to a bracket 163, so that the reservoir can be refilled in a sterile manner (Luer lock valves for sterile reservoir filling). Furthermore, a flexible tube 170 is provided, in particular in the form of a flexible feed/extraction tube, which extends from a valve 174 mounted on a bracket 173 on the outer side to the inner side of the container attachment 100 in order to provide for feed into or extraction from the interior of the cultivation container 50 in a sterile manner (Luer lock valve for sterile inoculation and/or extraction).

In a further embodiment of the invention (not shown), a further feed and/or extraction opening can optionally be provided, which extends to the inner side of the container attachment, in particular comprising a flexible tube (flexible feed/extraction tube), preferably a valve that may optionally be mounted on a bracket, and particularly preferably in combination with a transfer pump, in particular in order to couple a plurality of cultivation systems 10. A transfer pump may be provided in the form of a module comprising a plurality (e.g. four) of peristaltic pumps, which may be arranged on a base body, for example, such that the assembly corresponding to a cultivation system or a cultivation container fits on a shake flask holder.

The cultivation system 10 according to the invention is also referred to as a CAP (Controlled and Adjusted Processes) system. CAP means that, regardless of the shape of the cultivation vessel 50, both the in-situ sensor system and the actuators are integrated in the container attachment 100 that is in the form of a cap. Thus, a closed control loop is established that keeps the key process parameters in the optimum range in real time and in a sterile and reliable manner. A multi-sensor component according to German patent application 10 2019 117 446.5 is particularly suitable for the in-situ sensor system.

The CAP cultivation system according to the invention advantageously reduces the requirements on the periphery compared to prior art bioreactors. For example, in order to avoid a sterile workbench, provisions may be made so that the valve 174 in combination with a syringe forms a sterile connector for this purpose. In this embodiment, a cover film with a tab may be provided below the protective cap of the valve and the syringe. The connector sides can be disinfected and pressed together. The valve and the syringe may have a male/female design, for example, which allows the adjoining cover foils to be pulled out by the tabs without contamination, so that the transfer path is open. The same principle can be provided for the connection via the valves 164 of the reservoirs. In other words, at least one valve 164, 174 can generally be in the form of a sterile connector, e.g. sealed by a cover film, to provide for sterile connection. This also allows for inoculation, for example even after storage at e.g. −80° C., through an implementation involving a syringe or involving transfer using sterile fluid/air.

The cultivation container 50 itself may have the shape of a conventional bioreactor (optionally with flow breakers), with straight side walls. Shake flasks are preferred due to their design and availability. One design feature is the substance and heat transfer which can in particular be influenced by the number of baffles.

The CAP system may be prepared for cultivation using an autoclave and a sterile workbench. With the present invention, advantageously, this is also possible even without a sterile work station.

If sterile workbenches and autoclaves are used, the medium may be provided in a standard shake flask 50 and the CAP base 101 and reservoirs 140 can be fitted thereto. CAP base 101 is heat-resistant up to 141° C., optionally including the flexible tubes 160, 162, 170 mentioned above, which may be made of PP, for example, the reservoirs 140 or dispensing units 122, and the sensor components 114 or sensor units 112. The container attachment is thus capable of sealing the cultivation container, i.e. especially the shake flask, as sterile as a conventional shake flask cap.

Preferably, two dispensing units 122 with reservoirs 140 of different sizes are provided, which can be used in a flexible manner adapted to the cultivation.

In the case of heat-resistant feed and pH correction solutions, these solutions may also be provided in the reservoirs 140 and closed with lids 146D (see FIG. 8). Heat-resistant media may be provided in the shake flasks. Prepared in this way, autoclaving can then be performed, while the flexible tubes of the reservoirs can be clamped with hemostatic clamps, and subsequently inoculation may be performed in a sterile workbench.

Special Luer lock style ports may be provided to enable sterile safe working without a sterile work station. The Luer lock style ports include a Luer lock valve and optionally a flexible tube 160, 162 (e.g. made of PP) that can be extended through the lid 146D of the respective reservoir 140. Via the ports or valves, the reservoirs can be filled in a sterile manner with sterile filtered pH correction solution and feed solution.

A further port via which the flexible tube 170 (e.g. made of PP) is extended into the shake flask allows for sterile filling with sterile filled medium as well as sterile safe inoculation. The flexible tube 170 may also be extended as far as into the medium, for example for sampling purposes, repeated batch cultivation or continuous cultivation, in particular also in combination with a further flexible feed/extraction tube (not shown) that extends to the inner side of the container attachment.

The invention is particularly suitable for cultivation in an orbital shaker incubator which allows to adjust the mixing, temperature, and atmosphere (e.g. humidity or $CO_2$ concentration).

Brackets 163, 173 may be in the form of clip brackets. This allows for easy handling and fixation during cultivation in the shaking incubator, especially when using the flexible PP tube connection.

Mixing for substrate and heat transfer is also possible in combination with a magnetic stirrer and a stir bar, in particular a system-compatible one.

The configuration as shown in FIG. 5 already ensures sterility in the cultivation unit. An electronic module 132 (see FIG. 7) can then be fitted thereto without requirement for a sterile environment. Subsequently, a sensor unit 112 may be installed, which can be connected to the electronic module via a cable and a connector. The module includes a connection 180 for power supply and data transfer.

The connection may be routed to the interface of the shaking incubator or to a central unit. Such a central unit may integrate a connection of the cultivation units to a power supply by mains grid or rechargeable batteries, and/or to a process control system. The process control system can be visualized using an app for mobile devices. It is also possible to integrate the functions of this connection into the electronic module 132, however this may be dispensed with in order to keep the electronic module 132 compact and to keep its weight low and to avoid the risk of stability loss in the orbital shaker.

For implementation of a closed control loop which allows to keep the key process parameters in the optimum range in real time in a sterile and safe manner, the electronic module may include actuators 190 for pressure-controlled dosing integrated therein. In other words, the container attachment 100, the dispensing unit 122, and/or the electronic module 132 may comprise an actuator 190 for controlling the post flow of gas through a connection, in particular in the form of a flexible tube 160, between the reservoir and the inner side of the container attachment. Such an actuator 190 is in particular used for pressure-controlled dosing and may comprise a coil and a return spring in order to transfer a force to the flexible PP tubes.

As described above, the flexible PP tubes 160 extend from the lid 146D of the reservoirs into the shake flask 50. Atmospheric pressure can prevail in the shake flask via the sterile safe slot 106 between the shake flask 50 and the container attachment 100, which is common in the art. The outlet 144 of reservoirs 140 may be much narrower.

When the reservoirs 140 are filled via Luer lock valves 164, they are preferably filled first while the shake flask 50 is tilted such that displaced air can escape via the reservoir outlet 144.

For controlling the key parameters which can be captured in-situ in real time by the sensor unit 112, the dosing of the solutions provided in the reservoirs 140 can now be effected by driving the actuators 190. When the actuator 190 is retracted, dosing is effected via the reservoir outlet 144. When the flexible PP tube is blocked by the actuators 190, no feed solution or pH correction solution will be dosed since a negative pressure is established in the reservoir. In one embodiment, not shown, the reservoir outlet 144 is controlled by an actuator. For reasons of installation space, this may be associated with a smaller reservoir volume.

The invention claimed is:

1. A cultivation system, comprising:
   a cultivation container having an interior configured to hold a culture medium and an exterior, the cultivation container having a neck and an opening extending through the neck;
   a container attachment is placeable on the neck so as to close the opening in a sterile manner, the container attachment having an inner side and an outer side, the inner side facing the interior and the outer side facing the exterior when the container attachment is placed on the neck,
   wherein the container attachment comprises a port having a sensor unit at least partially arranged on the inner side of the container attachment, the sensor unit being configured to measure parameters in the interior of the cultivation container; and
   wherein the container attachment further comprises a port having a dispensing unit at least partially arranged on the inner side of the container attachment, the dispensing using comprising a reservoir for holding liquid and being configured to dispense liquid from the reservoir into the interior of the container.

2. The cultivation system of claim 1, wherein the cultivation container is a shake flask.

3. The cultivation system of claim 1, wherein the neck of the cultivation container has an annular shape; and/or wherein the container attachment has an annular slot for receiving the neck of the cultivation container; and/or wherein the container attachment has an outer collar forming part of the outer side of the container attachment and radially surrounding the neck of the cultivation container when the container attachment is placed on the neck of the cultivation container; and/or wherein the container attachment has an inner projection forming part of the inner side of the container attachment and protruding into the opening that extends through the neck of the cultivation container when the container attachment is placed on the neck of the cultivation container; and wherein the outer collar and the inner projection of the container attachment are formed monolithically.

4. The cultivation system of claim 1, wherein the cultivation container has a flat base for being placed on a supporting surface; and/or wherein the neck of the cultivation container extends vertically upwards when the cultivation container is placed on a supporting surface; and/or wherein the container attachment can be placed onto the neck of the cultivation container vertically from above and is designed to be held on the neck of the cultivation container by gravity.

5. The cultivation system of claim 1, wherein the cultivation container has a volume selected from a group consisting of less than 2801 milliliters, less than 1801 milliliters, less than 501 milliliters, less than 251 milliliters, and less than 126 milliliters; or wherein the cultivation container has a diameter selected from a group consisting of less than 22 centimeters, less than 21 centimeters, less than 14 centimeters, less than 12 centimeters, less than 9 centimeters, and less than 8 centimeters; or wherein the cultivation container has a height selected from a group consisting of less than 31 centimeters, less than 23 centimeters, less than 19 centimeters, less than 17 centimeters, less than 14 centimeters; or wherein the container attachment has an abutment surface and an annular slot, the abutment surface is located at the upper end of the annular slot and comes to rest on the cultivation container when the container attachment is placed on the cultivation container, and wherein the container attachment has a height as measured from said abutment surface selected from a group consisting of less than 14 centimeters, less than 10 centimeters, less than 5 centimeters, less than 4 centimeters, less than 3 centimeters, and less than 2 centimeters.

6. The cultivation system of claim 1, wherein the at least one dispensing unit of the container attachment comprises a reservoir for holding liquid, said reservoir comprising a lower reservoir section having an outlet opening for dispensing liquid and an upper reservoir section having a post flow opening for post flow of gas; and wherein the lower reservoir section is arranged or arrangeable on the inner side of the container attachment in order to allow liquid to be dispensed through the outlet opening into the interior of the cultivation container; and wherein the upper reservoir section is arranged or arrangeable on the outer side of the container attachment and is designed to have a larger width in order to define a stop when the dispensing unit and/or the reservoir is installed on a port of the container attachment.

7. The cultivation system of claim 6, wherein the container attachment and/or the dispensing unit comprise a connection in the form of a flexible tube, between the post flow opening of the upper reservoir section and the inner side of the container attachment in order to provide for post flow of gas, in a sterile manner, from the interior of the cultivation container when the container attachment is placed on the neck of the cultivation container.

8. The cultivation system of claim 6, wherein the upper reservoir section has a refill opening for refilling liquid; and wherein the container attachment and/or the dispensing unit comprise a connection in the form of a flexible tube, between the refill opening of the reservoir and a valve that is arranged or arrangeable on the outer side of the container attachment, to enable liquid to be refilled into the reservoir in a sterile manner; and wherein the container attachment and/or the dispensing unit have a bracket for releasably fixing the valve.

9. The cultivation system of claim 1, wherein the container attachment comprises a connection in the form of a flexible tube, between the inner side of the container attachment and a valve that is arranged or arrangeable on the outer side of the container attachment, to provide for feed into or extraction from the interior of the cultivation container, in a sterile manner, when the container attachment is placed on the neck of the cultivation container; and wherein the container attachment has a bracket for releasably fixing the valve.

10. The cultivation system of claim 1, wherein the at least one sensor unit of the container attachment is in the form of a biosensor unit for analyte-specific parameter measurement; or wherein the sensor unit or a further sensor unit of the container attachment, which is not a biosensor unit, is in the form of a luminophoric unit for luminescence-based parameter measurement; or wherein the sensor unit or a further sensor unit of the container attachment is in the form of an alternating field unit for dielectric-based parameter measurement; and/or wherein sensor unit or a further sensor unit of the container attachment is in the form of a transistor unit for field effect-based parameter measurement; or wherein the sensor unit is arranged or arrangeable on a front housing section of a sensor component such that the sensor unit is arrangeable on the inner side of the container attachment by installing the sensor component on a port of the container attachment to enable parameter measurement in the interior of the cultivation container when the container attachment is placed on the neck of the cultivation container.

11. The cultivation system of claim 1, wherein the container attachment comprises a plurality of sensor and/or dispensing units or corresponding ports, the sensor unit or a corresponding port and the at least one dispensing unit or a corresponding port, the sensor unit or a corresponding port and at least two dispensing units or corresponding ports.

12. A container attachment for being placed on a cultivation container, comprising:

an inner side and an outer side, the inner side facing the interior of the cultivation container and the outer side facing the exterior of the cultivation container when the container attachment is placed on the cultivation container, wherein the container attachment comprises a port having a sensor unit at least partially arranged on the inner side of the container attachment, the sensor unit being configured to measure parameters in the interior of the cultivation container; and wherein the container attachment comprises a port having a dispensing unit at least partially arranged on the inner side of the container attachment, the dispensing unit comprising a reservoir for holding liquid and being configured to dispense liquid from the reservoir into the interior of the container.

13. The container attachment of claim 12, wherein the container attachment has an annular slot for receiving a neck of the cultivation container; and/or wherein the container attachment has an outer collar which radially surrounds the neck of the cultivation container when the container attachment is placed on the cultivation container; and/or wherein the container attachment has an inner projection protruding into the neck of the cultivation container when the container attachment is placed on the cultivation container; and wherein the outer collar and the inner projection are formed monolithically.

14. The container attachment of claim 13, wherein the container attachment has an abutment surface that is located at the upper end of the annular slot and which comes to rest on the cultivation container when the container attachment is placed on the cultivation container, and wherein the container attachment has a height as measured from said abutment surface selected from a group consisting of less than 14 centimeters, less than 10 centimeters, less than 5 centimeters, less than 4 centimeters, less than 3 centimeters, and less than has 2 centimeters.

15. The container attachment of claim 12, wherein the container attachment can be placed onto the cultivation container vertically from above and is designed to be held on the cultivation container by gravity.

16. The container attachment of claim 12, wherein the dispensing unit comprises a reservoir for holding liquid, said reservoir comprising a lower reservoir section having an outlet opening for dispensing liquid and an upper reservoir section having a post flow opening for post flow of gas, and wherein the lower reservoir section is arranged or arrangeable on the inner side of the container attachment in order to allow liquid to be dispensed through the outlet opening into the interior of the cultivation container; and wherein the upper reservoir section is arranged or arrangeable on the outer side of the container attachment and is designed to have a larger width in order to define a stop when the dispensing unit and/or the reservoir is installed on a port of the container attachment.

17. The container attachment of claim 16, wherein the container attachment and/or the dispensing unit comprise a connection between the post flow opening of the upper reservoir section and the inner side of the container attachment in order to provide for post flow of gas from the interior of the cultivation container when the container attachment is placed on a neck of the cultivation container.

18. The container attachment of claim 12, wherein the reservoir has a refill opening for refilling liquid, and wherein the container attachment and/or the dispensing unit comprise a connection between the refill opening of the reservoir and a valve that is arranged or arrangeable on the outer side of the container attachment, to enable liquid to be refilled into the reservoir, and wherein the container attachment and/or the dispensing unit has a bracket for releasably fixing the valve.

19. The container attachment of claim 12, wherein the container attachment comprises a connection between the inner side of the container attachment and a valve that is arranged or arrangeable on the outer side of the container attachment, to provide for feed into or extraction from the interior of the cultivation container when the container attachment is placed on the cultivation container, and wherein the container attachment has a bracket for releasably fixing the valve.

20. The container attachment of claim 12, wherein the sensor unit is in the form of a biosensor unit for analyte-specific parameter measurement; or wherein the sensor unit or a further sensor unit of the container attachment, which is not a biosensor unit, is in the form of a luminophoric unit for luminescence-based parameter measurement; or wherein the sensor unit or a further sensor unit of the container attachment is in the form of an alternating field unit for dielectric-based parameter measurement; or wherein the sensor unit or a further sensor unit of the container attachment is in the form of a transistor unit for field effect-based parameter measurement; or wherein the sensor unit is arranged or arrangeable on a front housing section of a sensor component such that the sensor unit is arrangeable on the inner side of the container attachment by installing the sensor component on a port of the container attachment.

21. The container attachment of claim 12, wherein the container attachment comprises a plurality of sensors and/or dispensing units or a plurality of ports each having a corresponding dispensing unit.

* * * * *